(12) United States Patent
Askin et al.

(10) Patent No.: US 9,790,190 B2
(45) Date of Patent: Oct. 17, 2017

(54) PROCESS FOR MAKING HYDROXYLATED CYCLOPENTYLPYRIMIDINE COMPOUNDS

(71) Applicants: Array BioPharma Inc., Boulder, CO (US); Genentech, Inc., South San Francisco, CA (US)

(72) Inventors: David Askin, South San Francisco, CA (US); Chong Han, South San Francisco, CA (US); Jonathan W. Lane, Boulder, CO (US); Travis Remarchuk, South San Francisco, CA (US); Sagar Shakya, Boulder, CO (US); C. Gregory Sowell, South San Francisco, CA (US); Keith L. Spencer, Boulder, CO (US); Peter J. Stengel, Boulder, CO (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/593,064

(22) Filed: May 11, 2017

(65) Prior Publication Data

US 2017/0247337 A1 Aug. 31, 2017

Related U.S. Application Data

(62) Division of application No. 15/204,715, filed on Jul. 7, 2016, now Pat. No. 9,676,730, which is a division of application No. 14/401,087, filed as application No. PCT/US2013/041666 on May 17, 2013, now Pat. No. 9,416,110.

(60) Provisional application No. 61/785,122, filed on Mar. 14, 2013, provisional application No. 61/648,473, filed on May 17, 2012.

(51) Int. Cl.
*C07D 403/00* (2006.01)
*C07D 239/42* (2006.01)
*C07D 403/04* (2006.01)

(52) U.S. Cl.
CPC ......... *C07D 239/42* (2013.01); *C07D 403/04* (2013.01)

(58) Field of Classification Search
None
See application file for complete search history.

(56) References Cited

U.S. PATENT DOCUMENTS

| 7,169,928 | B2 | 1/2007 | Schwartz et al. |
| 8,063,050 | B2 | 11/2011 | Mitchell et al. |
| 9,278,917 | B2 | 3/2016 | Remarchuk et al. |
| 9,290,458 | B2 | 3/2016 | Chakravarty et al. |
| 9,309,204 | B2 | 4/2016 | Lane et al. |
| 9,315,471 | B2 | 4/2016 | Babu et al. |
| 9,416,110 | B2 | 8/2016 | Askin et al. |
| 9,505,725 | B2 | 11/2016 | Chakravarty et al. |
| 9,676,730 | B2 | 6/2017 | Askin et al. |
| 2008/0051399 | A1 | 2/2008 | Mitchell et al. |
| 2011/0281844 | A1 | 11/2011 | Schwartz et al. |
| 2012/0149684 | A1 | 6/2012 | Beight et al. |
| 2014/0121193 | A1 | 5/2014 | Katz et al. |
| 2015/0099880 | A1 | 4/2015 | Babu et al. |
| 2015/0099881 | A1 | 4/2015 | Lane et al. |
| 2015/0148559 | A1 | 5/2015 | Remarchuk et al. |

FOREIGN PATENT DOCUMENTS

| EP | 1188754 | 3/2002 |
| WO | 1995015684 | 6/1995 |
| WO | 1998044797 | 10/1998 |
| WO | 1998056234 | 12/1998 |
| WO | 2000052134 | 9/2000 |
| WO | 2001022963 | 4/2001 |
| WO | 2004108673 | 12/2004 |
| WO | 2008006040 | 1/2008 |
| WO | 2009047255 | 4/2009 |
| WO | 2010120935 | 10/2010 |
| WO | 2012009649 | 1/2012 |
| WO | 2012040258 | 3/2012 |
| WO | 2012177925 | 12/2012 |

(Continued)

OTHER PUBLICATIONS

Lane, et al., "Route Scouting and Early Process Development of a Challenging Cyclopentylpyrimidine Intermediate in Arry-452/Gdc-0068", Organic Reactions and Processes, Gordon Research Conference, Jul. 18, 2012.

(Continued)

*Primary Examiner* — Jeffrey H Murray
(74) *Attorney, Agent, or Firm* — Viksnins Harris Padys Malen LLP

(57) ABSTRACT

The invention provides processes for preparing a compound of formula I and salts thereof, wherein $R^1$ is defined herein, and compounds and intermediates of said formula.

23 Claims, No Drawings

(56) References Cited

FOREIGN PATENT DOCUMENTS

| WO | 2014127350 | 8/2014 |
| WO | 2014150395 | 9/2014 |

OTHER PUBLICATIONS

Lane, et al., "Synthesis of Akt Inhibitor Ipatasertib. Part 1. Route Scouting and Early Process Development of a Challenging Cyclopentylpyrimidine Intermediate", Org. Process Res. Dev. 18, 1641-1651 (2014).
Patent Cooperation Treaty, "International Searching Authority, Search Report and Written Opinion for PCT/US2013/041666", 9 pages, Jul. 18, 2013.
Remarchuk, et al., "Synthesis of Akt Inhibitor Ipatasertib. Part 2. Total Synthesis and First Kilogram Scale-up", Organic Process Research and Development 18, 1652-1666 (2014).

PROCESS FOR MAKING HYDROXYLATED CYCLOPENTYLPYRIMIDINE COMPOUNDS

PRIORITY OF INVENTION

This application is a divisional of U.S. patent application Ser. No. 15/204,715, filed Jul. 7, 2016, which is a divisional of U.S. patent application Ser. No. 14/401,087, filed Nov. 13, 2014, which has issued as U.S. Pat. No. 9,416,110, which is a 35 U.S.C. 371 national stage application of International Patent Application No. PCT/US2013/041666, filed on May 17, 2013, and claims priority to U.S. Provisional Application No. 61/648,473, filed on May 17, 2012 and U.S. Provisional Application No. 61/785,122, filed on Mar. 14, 2013, all of which are incorporated herein by reference in their entirety.

FIELD OF THE INVENTION

Disclosed herein are processes for making and purifying cyclopentylpyrimidine compounds with therapeutic activity, against diseases such as cancer, as inhibitors of AKT kinase activity.

BACKGROUND OF THE INVENTION

The Protein Kinase B/Akt enzymes are a group of serine/threonine kinases that are overexpressed in certain human tumors. International Patent Application Publication Number WO 2008/006040 and U.S. Pat. No. 8,063,050 discuss a number of inhibitors of AKT, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (GDC-0068). While processes described in WO 2008/006040 and U.S. Pat. No. 8,063,050 are useful in providing hydroxylated cyclopenta[d]pyrimidine compounds as AKT protein kinase inhibitors, alternative or improved processes are needed, including for large scale manufacturing of these compounds.

BRIEF SUMMARY OF THE INVENTION

Disclosed are processes for preparing, separating and purifying compounds detailed herein. Compounds provided herein include AKT protein kinase inhibitors, salts thereof, and intermediates useful in the preparation of such compounds.

One aspect includes a process that includes cyclizing a compound of formula II

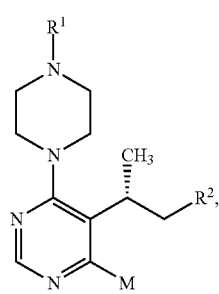

II or a salt thereof, to form a compound of formula I

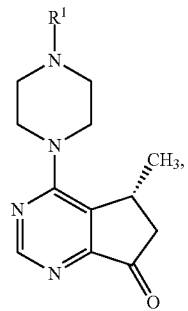

I or a salt thereof, wherein:

R$^1$ is hydrogen or an amino protecting group;

R$^2$ is —CN, —COOR$^a$ or —CONR$^a$R$^b$;

R$^a$ and R$^b$ are independently hydrogen, —OR$^c$, substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{3-8}$ cycloalkyl, substituted or unsubstituted phenyl or substituted or unsubstituted 3 to 12 membered heterocyclyl; or R$^a$ and R$^b$ are taken together with the atom to which they are attached to form a 3-7 membered heterocyclyl;

R$^c$ is independently hydrogen or optionally substituted $C_{1-12}$ alkyl; and

M is Li or Mg.

Another aspect includes a process that includes contacting a compound of formula III, or a salt thereof, with a magnesium or lithium metalating agent:

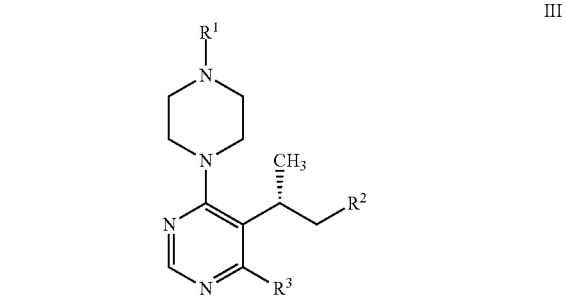

III wherein R$^3$ is bromo or iodo; to form the compound of formula I or a salt thereof.

Another aspect includes a process that includes contacting a compound of formula IV

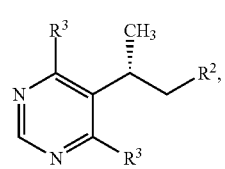

IV or a salt thereof, with a compound

Lv—N⌒N—R¹ or salt thereof, wherein Lv is a leaving group, and each $R^3$ is independently iodo or bromo, to form the compound of formula III or a salt thereof.

Another aspect includes a process that includes brominating or iodinating a compound of formula V $$\text{V}$$

[Structure of formula V with $R^4$, $CH_3$, $R^2$, $R^4$ on pyrimidine]

or a salt thereof, wherein $R^4$ is —Cl or —OH, to form a compound of formula IV.

Another aspect includes a compound of formula II $$\text{II}$$

[Structure of formula II with $R^1$, piperazine, pyrimidine, $CH_3$, $R^2$, M]

or a salt thereof, wherein:
$R^1$ is hydrogen or an amino protecting group;
$R^2$ is —CN, —COOR$^a$ or —CONR$^a$R$^b$;
$R^a$ and $R^b$ are independently hydrogen, —OR$^c$, substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{3-8}$ cycloalkyl, substituted or unsubstituted phenyl or substituted or unsubstituted 3 to 12 membered heterocyclyl; or
$R^a$ and $R^b$ are taken together with the atom to which they are attached to form a 3-7 membered heterocyclyl;
$R^c$ is independently hydrogen or optionally substituted $C_{1-12}$ alkyl; and
M is Li or Mg.

Another aspect includes a compound of formula III $$\text{III}$$

[Structure of formula III with $R^1$, piperazine, pyrimidine, $CH_3$, $R^2$, $R^3$]

or a salt thereof, wherein:
$R^1$ is hydrogen or an amino protecting group;
$R^2$ is —CN, —COOR$^a$ or —CONR$^a$R$^b$;
$R^a$ and $R^b$ are independently hydrogen, —OR$^b$, substituted or unsubstituted alkyl, substituted or unsubstituted alkenyl, substituted or unsubstituted alkynyl, substituted or unsubstituted cycloalkyl, substituted or unsubstituted phenyl or substituted or unsubstituted heterocyclyl; or
$R^a$ and $R^b$ are taken together with the atom to which they are attached to form a 3-7 membered heterocyclyl; and
$R^3$ is bromo or iodo.

Another aspect includes a compound of formula IV $$\text{IV}$$

[Structure of formula IV with $R^3$, $CH_3$, $R^2$, $R^3$ on pyrimidine]

or a salt thereof, wherein:
$R^2$ is —CN, —COOR$^a$ or —CONR$^a$R$^b$; and each $R^3$ is independently iodo or bromo.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, tem usage, described techniques, or the like, this application controls.

"Acyl" means a carbonyl containing substituent represented by the formula —C(O)—R in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are independently optionally substituted and as defined herein. Acyl groups include alkanoyl (e.g., acetyl), aroyl (e.g., benzoyl), and heteroaroyl (e.g., pyridinoyl).

The term "alkyl" as used herein refers to a saturated linear or branched-chain monovalent hydrocarbon radical of one to twelve carbon atoms, and in another embodiment one to six carbon atoms, wherein the alkyl radical may be optionally substituted independently with one or more substituents described herein. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms, and in another embodiment two to six carbon atoms, with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), 1-propenyl, 1-buten-1-yl, 1-buten-2-yl, and the like.

The term "alkynyl" as used herein refers to a linear or branched monovalent hydrocarbon radical of two to twelve carbon atoms, and in another embodiment two to six carbon atoms, with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$C≡CH).

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

"Amino" means primary (i.e., —NH$_2$), secondary (i.e., —NRH), tertiary (i.e., —NRR) and quaternary (i.e., —N$^+$RRRX$^-$) amines, that are optionally substituted, in which R is independently alkyl, alkoxy, a cycloalkyl, a heterocyclyl, cycloalkyl, -substituted alkyl or heterocyclyl-substituted alkyl wherein the alkyl, alkoxy, cycloalkyl and heterocyclyl are as defined herein Particular secondary and tertiary amines are alkylamine, dialkylamine, arylamine, diarylamine, aralkylamine and diaralkylamine wherein the alkyls and aryls are as herein defined and independently optionally substituted. Particular secondary and tertiary amines are methylamine, ethylamine, propylamine, isopropylamine, phenylamine, benzylamine dimethylamine, diethylamine, dipropylamine and diisopropylamine.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms, and in another embodiment three to eight carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, cyclohexenyl, cyclohexadienyl, cycloheptenyl, and the like. Bicyclic carbocycles include those having 7 to 12 ring atoms arranged, for example, as a bicyclo [4,5], [5,5], [5,6] or [6,6] system, or as bridged systems such as bicyclo[2.2.1]heptane, bicyclo[2.2.2]octane, and bicyclo [3.2.2]nonane. The cycloalkyl may be optionally substituted independently with one or more substituents described herein.

The term "aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "hetercyclyl" and "heterocyclic ring" as used herein are used interchangeably and refer to a saturated or partially unsaturated carbocyclic radical of 3 to 12 membered ring atoms in which at least one ring atom is a heteroatom independently selected from nitrogen, oxygen and sulfur, the remaining ring atoms being C, where one or more ring atoms may be optionally substituted independently with one or more substituents described below. One embodiment includes heterocycles of 3 to 7 membered ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (═O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

"Leaving group" refers to a portion of a first reactant in a chemical reaction that is displaced from the first reactant in the chemical reaction. Examples of leaving groups include, but are not limited to, hydrogen, halogen, hydroxyl groups, sulfhydryl groups, amino groups (for example —NRR, wherein R is independently alkyl, alkenyl, alkynyl, cycloalkyl, phenyl or heterocyclyl and R is independently optionally substituted), silyl groups (for example —SiRRR, wherein R is independently alkyl, alkenyl, alkynyl, cycloalkyl, phenyl or heterocyclyl and R is independently optionally substituted), —N(R)OR (wherein R is independently alkyl, alkenyl, alkynyl, cycloalkyl, phenyl or heterocyclyl and R is independently optionally substituted), alkoxy groups (for example —OR, wherein R is independently alkyl, alkenyl, alkynyl, cycloalkyl, phenyl or heterocyclyl and R is independently optionally substituted), thiol groups (for example —SR, wherein R is independently alkyl, alkenyl, alkynyl, cycloalkyl, phenyl or heterocyclyl and R is independently optionally substituted), sulfonyloxy groups (for example —OS(O)$_{1-2}$R, wherein R is independently alkyl, alkenyl, alkynyl, cycloalkyl, phenyl or heterocyclyl and R is independently optionally substituted), sulfamate groups (for example —OS(O)$_{1-2}$NRR, wherein R is independently alkyl, alkenyl, alkynyl, cycloalkyl, phenyl or heterocyclyl and R is independently optionally substituted), carbamate groups (for example —OC(O)$_2$NRR, wherein R is independently alkyl, alkenyl, alkynyl, cycloalkyl, phenyl or heterocyclyl and R is independently optionally substituted), and carbonate groups (for example —OC(O)$_2$RR, wherein R is independently alkyl, alkenyl, alkynyl, cycloalkyl, phenyl or heterocyclyl and R is independently optionally substituted). Example sulfonyloxy groups include, but are not limited to, alkylsulfonyloxy groups (for example methyl sulfonyloxy (mesylate group) and trifluoromethylsulfonyloxy (triflate group)) and aryl sulfonyloxy groups (for example p-toluenesulfonyloxy (tosylate group) and p-nitrosulfonyloxy (nosylate group)). Other examples of leaving groups include substituted and unsubstituted amino groups, such as amino, alkylamino, dialkylamino, hydroxylamino, alkoxylamino, N-alkyl-N-alkoxyamino, acylamino, sulfonylamino, and the like.

"Amino-protecting group" as used herein refers to groups commonly employed to keep amino groups from reacting during reactions carried out on other functional groups. Examples of such protecting groups include carbamates, amides, alkyl and aryl groups, imines, as well as many N-heteroatom derivatives which can be removed to regenerate the desired amine group. Particular amino protecting groups are Ac (acetyl), trifluoroacetyl, phthalimide, Bn (benzyl), Tr (triphenylmethyl or trityl), benzylidenyl, p-toluenesulfonyl, Pmb (p-methoxybenzyl), Boc (tert-butyloxycarbonyl), Fmoc (9-fluorenylmethyloxycarbonyl) and Cbz (carbobenzyloxy). Further examples of these groups are found in: Wuts, P. G. M. and Greene, T. W. (2006) Frontmatter, in Greene's Protective Groups in Organic Synthesis, Fourth Edition, John Wiley & Sons, Inc., Hoboken, N.J., USA. The term "protected amino" refers to an amino group substituted with one of the above amino-protecting groups.

The term "substituted" as used herein means any of the above groups (e.g., alkyl, alkylene, alkenyl, alkynyl, cycloalkyl, aryl, heterocyclyl and heteroaryl) wherein at least one hydrogen atom is replaced with a substituent. In the case of an oxo substituent ("=O") two hydrogen atoms are replaced. "Substituents" within the context of this invention include, but are not limited to, halogen, hydroxy, oxo, cyano, nitro, amino, alkylamino, dialkylamino, alkyl, alkenyl, alkynyl, cycloalkyl, alkoxy, substituted alkyl, thioalkyl, haloalkyl (including perhaloalkyl), hydroxyalkyl, aminoalkyl, substituted alkenyl, substituted alkynyl, substituted cycloalkyl, aryl, substituted aryl, heteroaryl, substituted heteroaryl, heterocycle, substituted heterocycle, —NR$^e$R$^f$, —NR$^e$C(=O)R$^f$, —NR$^e$C(=O)NR$^e$R$^f$, —NR$^e$C(=O)OR$^f$—NR$^e$SO$_2$R$^f$, —OR$^e$, —C(=O)R$^e$—C(=O)OR$^e$, —C(=O)NR$^e$R$^f$, —OC(=O)NR$^e$R$^f$, —SR$^e$, —SOR$^e$, S(=O)$_2$R$^e$, —OS(=O)$_2$R$^e$, —S(=O)$_2$OR$^e$, wherein R$^e$ and R$^f$ are the same or different and independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycle, substituted heterocycle.

The term "halo" or "halogen" as used herein means fluoro, chloro, bromo or iodo.

The term "a" as used herein means one or more.

Reference to "about" a value or parameter herein includes (and describes) embodiments that are directed to that value or parameter per se and in one embodiment plus or minus 20% of the given value. For example, description referring to "about X" includes description of "X".

"Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}C$ or $^{14}C$ carbon atom, or one or more nitrogen atoms are replaced by a $^{15}N$ nitrogen atom, or one or more sulfur atoms are replaced by a $^{33}S$, $^{34}S$ or $^{36}S$ sulfur atom, or one or more oxygen atoms are replaced by a $^{17}O$ or $^{18}O$ oxygen atom are within the scope of this invention.

One aspect provides a process comprising cyclizing a compound of formula II

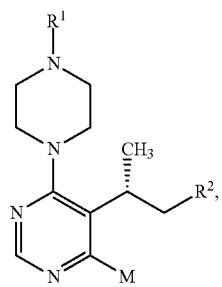

II or a salt thereof, to form a compound of formula I

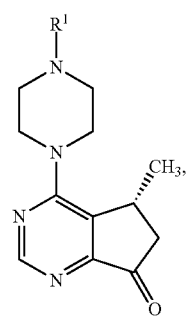

I or a salt thereof, wherein:
$R^1$ is hydrogen or an amino protecting group;
$R^2$ is —CN, —COOR$^a$ or —CONR$^a$R$^b$;
$R^a$ and $R^b$ are independently hydrogen, —OR$^c$, substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{3-8}$ cycloalkyl, substituted or unsubstituted phenyl or substituted or unsubstituted 3-12 memered heterocyclyl; or
$R^a$ and $R^b$ are taken together with the atom to which they are attached to form a 3-7 membered heterocyclyl;
$R^c$ is independently hydrogen or optionally substituted $C_{1-12}$ alkyl; and
M is Li or Mg.

Another aspect includes the compound of formula I or a salt thereof produced according to the process comprising cyclizing a compound of formula II or a salt thereof.

Another aspect provides a process comprising, contacting a compound of formula III

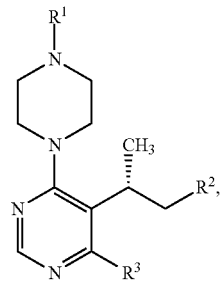

III or a salt thereof, wherein:
$R^1$ is hydrogen or an amino protecting group;
$R^2$ is —CN, —COOR$^a$ or —CONR$^a$R$^b$;
$R^a$ and $R^b$ are independently hydrogen, —OR$^c$, substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{3-8}$ cycloalkyl, substituted or unsubstituted phenyl or substituted or unsubstituted 3 to 12 membered heterocyclyl; or
$R^a$ and $R^b$ are taken together with the atom to which they are attached to form a 3-7 membered heterocyclyl;
$R^c$ is independently hydrogen or optionally substituted $C_{1-12}$ alkyl; and
$R^3$ is bromo or iodo;
with a metalating agent comprising magnesium or lithium, to form a compound of formula I or a salt thereof.

Another aspect includes the compound of formula I or II, or a salt thereof, produced according to the process comprising contacting a compound of formula III with a metalating agent comprising magnesium or lithium.

In another embodiment, the above processes further comprise contacting a compound of formula IV:

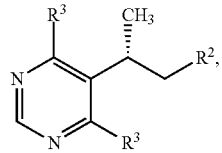

IV or a salt thereof, with a compound

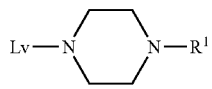

or salt thereof, to form a compound of formula III wherein:
$R^1$ is hydrogen or an amino protecting group;
$R^2$ is —CN, —COOR$^a$ or —CONR$^a$R$^b$;
$R^a$ and $R^b$ are independently hydrogen, —OR$^c$, substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{3-8}$ cycloalkyl, substituted or unsubstituted phenyl or substituted or unsubstituted 3 to 12 membered heterocyclyl; or
$R^a$ and $R^b$ are taken together with the atom to which they are attached to form a 3-7 membered heterocyclyl;
$R^c$ is independently hydrogen or optionally substituted $C_{1-12}$ alkyl; and
each $R^3$ is independently bromo or iodo; and
Lv is a leaving group.

Another aspect includes the compound of formula III, or a salt thereof, produced according to the process comprising contacting a compound of formula IV or a salt thereof, with a compound

or salt thereof.

In another embodiment, the above processes further comprise brominating or iodinating a compound of formula V

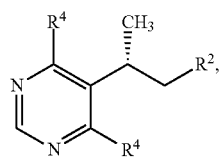

or a salt thereof to form a compound of formula IV or salt thereof, wherein $R^4$ is —Cl or —OH.

In one embodiment, the above processes further comprise brominating a compound of formula V, or a salt thereof, wherein $R^4$ is —OH.

In one embodiment, the above brominating further comprises contacting the compound of formula V, or a salt thereof, with a brominating agent to form a compound of formula IV, or salt thereof, wherein $R^3$ in formula IV is Br.

Brominating agents include, for example, PBr$_3$, PBr$_5$, O═PBr$_3$, P(OH)Br$_3$, Br$_2$ (in one example with a phosphine, such as PR$_3$ wherein R is an alkyl, cycloalkyl, aryl or heterocyclyl group), HBr, O═SBr$_2$, other bromide salts such as NaBr, KBr and CuBr$_2$ (in one example with fluorinating agents such as 1-chloromethyl-4-fluoro-1,4-diazoniabicyclo[2.2.2]octane bis(tetrafluoroborate) or Selectfluor®), and hexabromoacetone (in one example with an alkyltribromoacetate such as ethyltribromoacetate).

In one embodiment, the brominating agent comprises bromine and phosphorous, for example, PBr$_3$, PBr$_5$, O═PBr$_3$, P(OH)Br$_3$ and Br$_2$ in combination with a phosphine, such as PR$_3$ wherein R is an alkyl, cycloalkyl, aryl or heterocyclyl group.

In one embodiment, the above processes further comprise iodinating a compound of formula V, wherein $R^4$ is —Cl.

In one embodiment, the above iodinating further comprises contacting the compound of formula V, or a salt thereof, with an iodinating agent to form a compound of formula IV, or salt thereof, wherein $R^3$ in formula IV is I.

Iodinating agents include, for example, salts of iodide, such as NaI, KI or HI (in one example, generated in situ from an iodide salt and acid, such as sodium or potassium iodide with acid such as methanesulfonic acid).

Another aspect includes the compound of formula IV, or a salt thereof, produced according to the process comprising brominating or iodinating a compound of formula V.

In certain embodiments, when $R^1$ of formula I is an amino protecting group, the process further comprises, deprotecting the amino protecting group to provide a compound of the formula I where $R^1$ is H. In one example, $R^1$ is tert-butoxycarbonyl (Boc) and the process further comprises removing the Boc group by contacting the compound of formula I with an acid, for example hydrochloric, sulfuric, trifluoromethanesulfonic, or trifluoroacetic acid.

In certain embodiments, $R^1$ is an amino protecting group, for example, a removable carbamoyl group (e.g., tert-butoxycarbonyl and benzyloxycarbonyl). In some embodiments, $R^1$ of formula (II) and/or formula (I) is a substituted acyl group such as a substituted —C(O)-alkyl.

In certain embodiments, $R^1$ is —C(O)—R$^d$ or —C(O)OR$^d$, and $R^d$ is independently hydrogen, substituted or unsubstituted alkyl, substituted or unsubstituted alkenyl, substituted or unsubstituted alkynyl, substituted or unsubstituted cycloalkyl, substituted or unsubstituted phenyl or substituted or unsubstituted heterocyclyl.

In certain embodiments, $R^c$ is $C_{1-6}$ alkyl or hydrogen, wherein said alkyl is optionally substituted by oxo, halo or phenyl.

In certain embodiments, $R^d$ is $C_{1-6}$ alkyl or hydrogen, wherein said alkyl is optionally substituted by oxo, halo or phenyl. In certain embodiments, $R^d$ is tert-butyl.

In certain embodiments, $R^1$ is hydrogen.
In certain embodiments, $R^2$ is —COOR$^a$ or —CONR$^a$R$^b$.
In certain embodiments, $R^2$ is —COOH or —COOCH$_3$.
In certain embodiments, $R^2$ is —C(O)N(R$^a$)OR$^b$. In certain embodiments, $R^2$ is —C(O)N(CH$_3$)OCH$_3$.
In certain embodiments, $R^2$ is —CN, —COOH or —CONR$^a$R$^b$. In certain embodiments, $R^2$ is —COOMe or —COOEt. In certain embodiments, $R^2$ is —COOPr.

In certain embodiments, $R^a$ and $R^b$ are independently hydrogen, —OR$^c$, substituted or unsubstituted alkyl, substituted or unsubstituted alkenyl, substituted or unsubstituted alkynyl, substituted or unsubstituted cycloalkyl, substituted or unsubstituted phenyl or substituted or unsubstituted heterocyclyl.

In certain embodiments, $R^a$ and $R^b$ are independently hydrogen, $C_{1-6}$ alkyl or —O($C_{1-6}$ alkyl).

In certain embodiments, $R^a$ and $R^b$ are taken together with the atom to which they are attached to form a 3-7 membered heterocyclyl.

In certain embodiments, $R^a$ and $R^b$ are independently hydrogen or $C_{1-6}$ alkyl, wherein said alkyl is optionally substituted by oxo, halo or phenyl.

In certain embodiments, $R^a$ and $R^b$ are methyl.
In certain embodiments, $R^a$ and $R^b$ are taken together with the atom to which they are attached to form a morpholinyl group.

In certain embodiments, M is Mg.
In certain embodiments, M is Li.

In certain embodiments, $R^3$ is iodo. In another embodiment, $R^3$ is bromo.

In certain embodiments, $R^4$ is OH. In certain embodiments, $R^4$ is Cl.

In some embodiments, the metalating agent comprises one or more of lithium and magnesium. In some embodiments, the metalating agent is an organomagnesium compound such as a Grignard reagent (e.g., a $C_1$-$C_6$ alkylmagnesium halide, for example, iPrMgCl.) In some embodiments, the metalating agent is an organolithium compound such as a $C_1$-$C_6$ alkyllithium (e.g., n-butyllithium and t-butyllithium).

In some embodiments, the metalating agent is one or more of (i) LiR and (ii) $MgR_2$, wherein each R is independently halogen, optionally substituted $C_{1-6}$ alkyl, optionally substituted $C_{3-7}$ cycloalkyl, optionally substituted aryl, optionally substituted heteroaryl, or optionally substituted and herterocyclyl, or two R groups are taken together with the atom to which they are attached to form a 5-7 membered, optionally substituted ring. In some embodiments, each R is independently halogen, optionally substituted $C_{1-6}$ alkyl or optionally substituted $C_{3-7}$ cycloalkyl.

In one aspect, the process for preparing a compound of formula I, or a salt thereof, from a compound of formulae II or III may be carried out in an ethereal or hydrocarbon solvent or a mixture of these solvents. (e.g., tetrahydrofuran (THF), methyl tert-butyl ether (MTBE), cyclopentyl methyl ether (CPME), diethyl ether, diisopropyl ether, diphenyl ether, toluene, ethylbenzene, xylene, cumene, pentane or heptane). Other suitable conditions may be used (e.g., reaction temperature at or below 20° C., such as at about −10° C., or at about −78° C.), carrying out the reaction under substantially anhydrous conditions (for example, less than about 100 ppm, 50 ppm or less than about 10 ppm water), and carrying out the reaction under an inert atmosphere, for example, under a helium, neon, argon or nitrogen atmosphere). In a particular variation, a process for preparing a compound of formula I, or a salt thereof, from a compound of formulae II or III is carried out under nitrogen atmosphere in THF at a temperature of between about −25° C. and about −5° C., or at about −10±2° C., under anhydrous conditions.

In another embodiment, compounds of formula I are used in the preparation of inhibitors of AKT kinase for treating diseases and disorders responsive to the inhibition of AKT, as described in U.S. Pat. No. 8,063,050 to Mitchell, et al.

Another aspect includes a process of producing a compound of formula 2.2, or salt thereof,

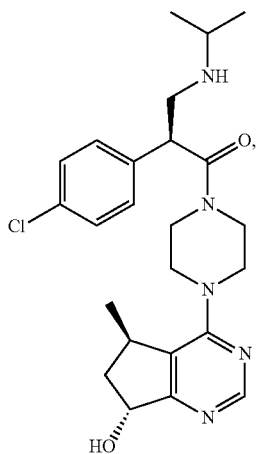

comprising reducing stereoselectively a compound of formula I, or salt thereof,

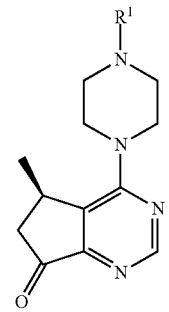

to form a compound of formula 2.1, or salt thereof,

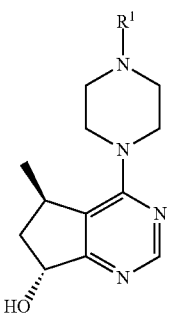

and reacting the compound of formula 2.1 or salt thereof with a compound of the formula

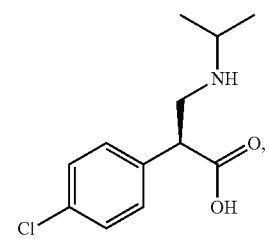 [SMILES: CC(C)NC[C@@H](C(=O)O)c1ccc(Cl)cc1]

or salt thereof, to form a compound of formula 2.2.

Another aspect includes the compound of formula 2.2 or salt thereof produced according to the process comprising reducing stereoselectively a compound of formula I, or salt thereof, to form a compound of formula 2.1, or salt thereof, and reacting the compound of formula 2.1 or salt thereof with a compound of the formula

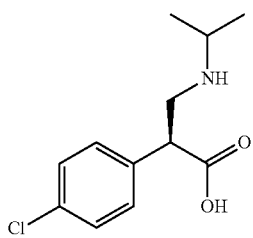 [SMILES: CC(C)NC[C@@H](C(=O)O)c1ccc(Cl)cc1]

or salt thereof.

The compounds detailed herein may contain one or more chiral centers. Accordingly, if desired, such compounds can be prepared or isolated as pure stereoisomers (such as individual enantiomers or diastereomers, or as stereoisomer-enriched mixtures). All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic or stereoisomer-enriched mixtures of such compounds can be separated using, for example, chiral column chromatography, chiral resolving agents, and the like.

For illustrative purposes, Scheme 1 shows a general method for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Scheme and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

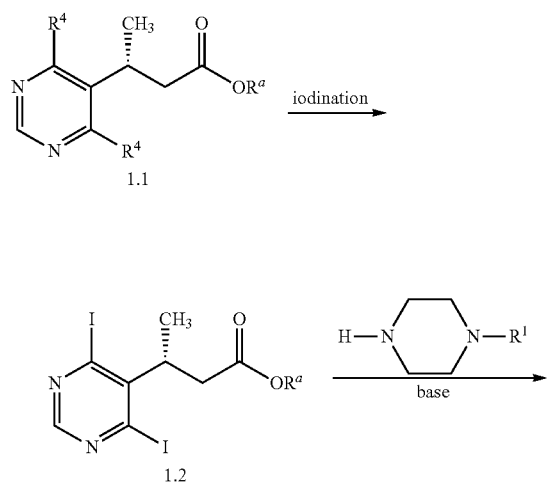

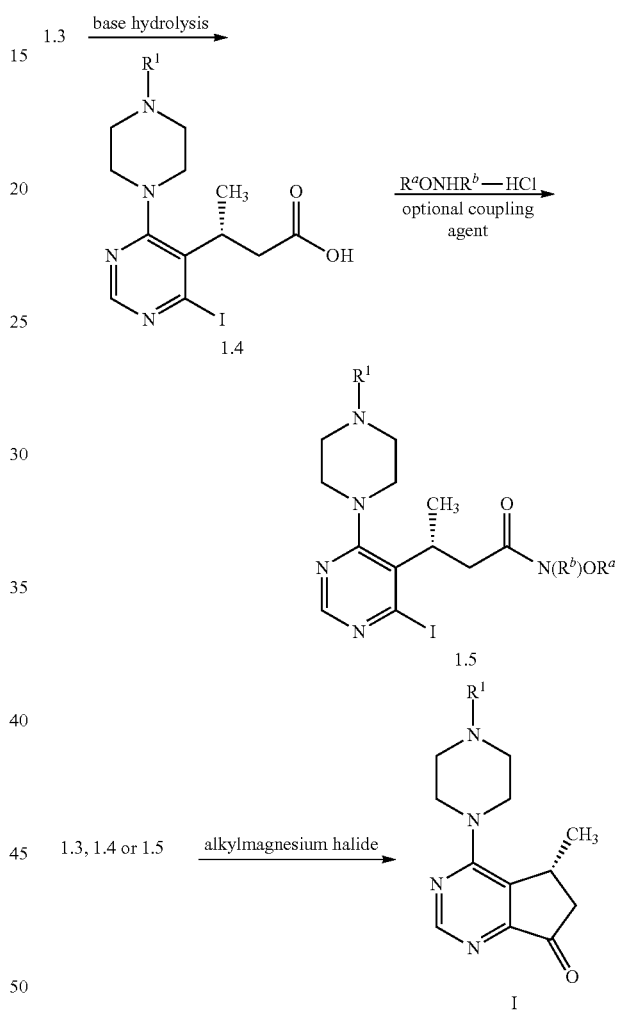

Scheme 1 illustrates a method for making a compound of the formula I, where $R^1$, $R^a$ and $R^b$ are independently defined as above for formula I. Reaction of compound 1.1 with an iodination agent (e.g., iodide salt, such as NaI and optionally with an acid), gives diiodopyrimidine 1.2, which reacts with a mono-protected piperazine to afford methyl ester 1.3. The methyl ester is coverted to an amide 1.5 via the acid intermediate 1.4 prepared by base hydrolysis of the ester. Amide 1.5 is metalated with a metalating agent, such a Grignard reagent (e.g., $^i$PrMgCl), and cyclized to form cyclopentyl ketone I.

Another aspect provides the use of compounds of formula I as intermediates for preparing pharmaceutically active compounds, such as the AKT inhibitors described in U.S. Pat. No. 8,063,050, issued Nov. 22, 2011 to Mitchell. For example, as shown below in Scheme 2, compounds of formula I can be used to prepare (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one, as described in U.S. Pat. No. 8,063,050, issued Nov. 22, 2011, as described, for example, in Example 14, which is incorporated herein by reference.

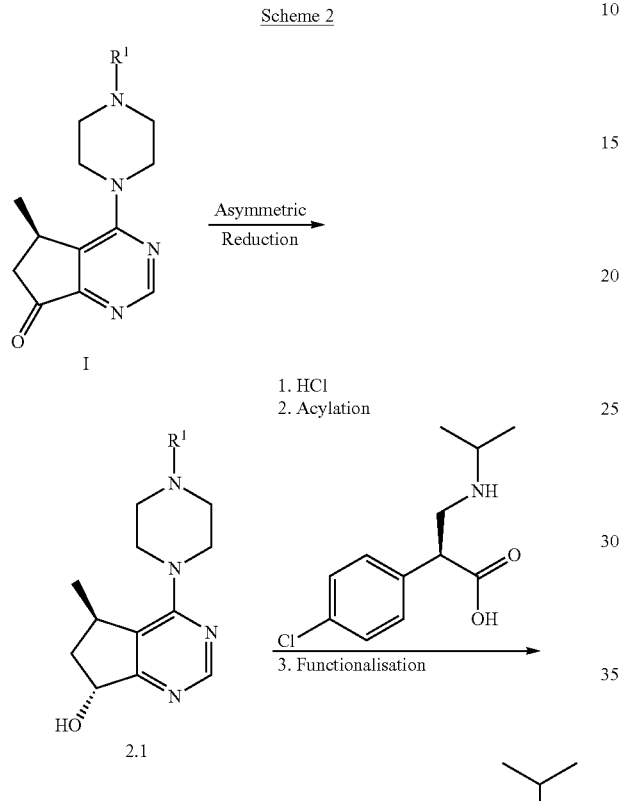

Scheme 2 illustrates a method for making a compound of formula 2.2. Asymmetric reduction of compounds of formula I give compounds of formula 2.1, wherein $R^1$ defined above for formula I. When $R^1$ is a protecting group, for example a Boc group, compound 2.1 can then be reacted with HCl, acylated and functionalized, for example by further deprotection, to give compound 2.2.

Another aspect includes a product produced by any process, scheme or example provided herein.

EXAMPLES

The invention can be further understood by reference to the following examples, which are provided by way of illustration and are not meant to be limiting.

Abbreviations used herein are as follows:
Aq.: aqueous
DIPA: diisopropylamine
DIPEA: diisopropylethylamine
MTBE: methyl t-butyl ether
TMSCl: chlorotrimethylsilane
MsDPEN: N-methanesulfonyl-1,2-diphenylethylenediamine
TsDACH: N-(p-toluenesulfonyl)-1,2-diaminocyclohexane
Dppp: 1,3-Bis(diphenylphosphino)propan
NMM: 4-methylmorpholine
PhME: toluene
CPME: Cyclopentyl methyl ether
DBU: 1,8-Diazobicyclo[5,40]undec-7-ene
CDI: 1,1'-carbonyldiimidazole

Example 1

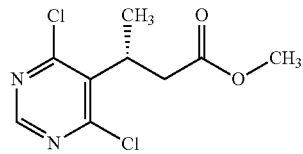

(R)-methyl 3-(4,6-dichloropyrimidin-5-yl)butanoate

Into a mixture of (R)-methyl 3-(4,6-dihydroxypyrimidin-5-yl)butanoate (1.00 kg, 4.70 mol), toluene (4.00 L), and 2,6-lutidine (0.550 L, 4.70 mol) was added phosphorous oxychloride (0.960 L, 10.6 mol) at 50° C. slowly. The mixture was stirred at 70° C. for 24 h. The solution was cooled to 0° C. To the mixture was slowly added 20% aqueous sodium hydroxide (about 40.0 mol, 1.60 kg in 8.00 L $H_2O$) while maintaining the internal temperature below 30° C., to obtain a final pH value between 5 and 6. Ethyl acetate (2.50 L) was added, stirred for 0.5 h, and then the layers were separated. The aqueous phase was extracted with ethyl acetate (3×1.00 L). The organics were combined and washed with 1 N hydrochloric acid (2×2.50 L), and brine (2.50 L). The organic layers were combined and dried over sodium sulfate and filtered through a glass fiber filter. The solution was concentrated to about 3.00 mL/g, and diluted with acetonitrile to about 7.00 mL/g. The sequence was repeated two times to remove residue ethyl acetate and toluene (confirmed by $^1H$ NMR analysis). The remaining crude solution was used directly for next step without further purification or isolation. $^1H$ NMR (300 MHz, $CDCl_3$) δ 8.62 (s, 1H), 4.15 (ddq, J=8.1, 7.2, 7.2 Hz, 1H), 3.64 (s, 3H), 3.08 (dd, J=16.5, 8.1 Hz, 1H), 2.86 (dd, J=16.5, 7.2 Hz, 1H), 1.45 (d, J=7.2 Hz, 3H). HRMS calcd. For $C_9H_{11}Cl_2N_2O_2$ [M+H]+: 249.0192, found 249.0190.

Example 2

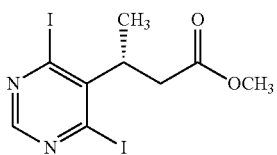

(R)-methyl 3-(4,6-diiodopyrimidin-5-yl)butanoate

Into a solution of (R)-methyl 3-(4,6-dichloropyrimidin-5-yl)butanoate (36.0 g, 145 mmol) in acetonitrile (540 mL) was added sodium iodide (152 g, 1.02 mol). The mixture was stirred at 25° C. for 30 min and then cooled to about 5° C. Methanesulfonic acid (9.41 mL, 1.00 equiv) was added over 5 min. The mixture was agitated at about 5° C. for 3 h. The reactor was cooled to about 5° C. and N,N-diisopropylethylamine (20.3 mL, 116 mmol) was added. The mixture was agitated for 1 h while warming the mixture to 20° C. Saturated sodium sulfite solution was added until no further color change was observed to remove the iodine. Water (540 mL) was added and the pH was adjusted to between about 5 and 7. The biphasic mixture was concentrated under reduced pressure at a temperature of less than 40° C. to remove acetonitrile. The aqueous suspension was filtered to give 48.8 g (78% yield) of off-white solid product. $^1$H NMR (300 MHz, CDCl$_3$) δ 8.21 (s, 1H), 4.02 (ddq, J=7.8, 7.5, 7.2 Hz, 1H), 3.67 (s, 3H), 3.18 (dd, J=16.5, 7.8 Hz, 1H), 2.91 (dd, J=16.5, 7.5 Hz, 1H), 1.47 (d, J=7.2 Hz, 3H). HRMS calcd. For $C_9H_{11}I_2N_2O_2$ [M+H]+: 432.8904, found 432.8906.

Example 3

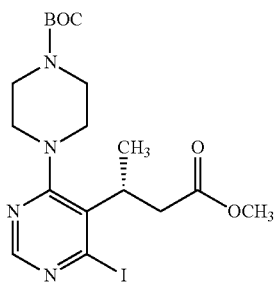 [SMILES: COC(=O)C[C@@H](C)c1c(I)ncnc1N1CCN(C(=O)OC(C)(C)C)CC1]

(R)-tert-butyl 4-(6-iodo-5-(4-methoxy-4-oxobutan-2-yl)pyrimidin-4-yl)piperazine-1-carboxylate Into a solution of (R)-methyl 3-(4,6-diiodopyrimidin-5-yl)butanoate (212 g, 491 mmol) and Boc-piperazine (101 g, 540 mmol) in methanol (424 mL) was added N,N-diisopropylethylamine (94.3 mL, 540 mmol). The mixture was heated at 60° C. for 24 h. Methanol was distilled off under reduced pressure below 40° C. To the mixture was added 318 mL of tetrahydrofuran. The above solvent swap process was repeated twice. To the mixture were added 424 mL of tetrahydrofuran, 212 mL of saturated aqueous ammonium chloride, and 21.2 mL of water. The organic layer was washed with 212 mL (1.00 vol.) of saturated aqueous ammonium chloride. This tetrahydrofuran solution was used for next step without further purification (91% weight assay yield). $^1$H NMR (300 MHz, CDCl$_3$) δ 8.25 (s, 1H), 3.80-3.67 (m, 1H), 3.65 (s, 3H), 3.60-3.56 (m, 4H), 3.21-3.18 (m, 4H), 3.14 (dd, J=16.2, 9.0 Hz, 1H), 2.81 (dd, J=16.2, 5.7 Hz, 1H), 1.48 (s, 9H), 1.47 (d, J=7.2 Hz, 3H). HRMS calcd. For $C_{18}H_{28}IN_4O_4$ [M+H]+: 491.1150, found 491.1154.

Example 4

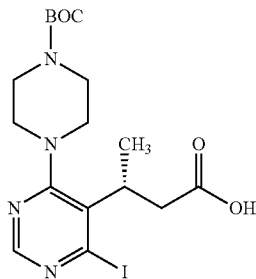 [SMILES: C[C@H](CC(=O)O)c1c(I)ncnc1N1CCN(C(=O)OC(C)(C)C)CC1]

(R)-3-(4-(4-(tert-butoxycarbonyl)piperazin-1-yl)-6-iodo-pyrimidin-5-yl)butanoic acid Into a solution of (R)-tert-butyl 4-(6-iodo-5-(4-methoxy-4-oxobutan-2-yl)pyrimidin-4-yl)piperazine-1-carboxylate (219 g, 0.447 mol) in tetrahydrofuran (657 mL) was added a solution of lithium hydroxide monohydrate (56.2 g, 1.34 mol) in 329 mL of water at 25° C. The mixture was stirred at 25° C. for 5 h. The bottom aqueous layer was discarded. The mixture was acidified with 1 N hydrochloric acid at 5° C. to give a final pH value of between about 1 to 2. The layers were separated. The top layer was then extracted with isopropyl acetate (440 mL×3), combined with the bottom layer, and washed with water (220 mL×2). The solvents was distilled off at reduced pressure below 50° C. The residual isopropyl acetate was azeotroped off with heptane under reduced pressure below 50° C. Product gradually precipitated out and was filtered to give an off-white to light yellow powder (196 g, 84% yield). $^1$H NMR (300 MHz, CDCl$_3$) δ 8.27 (s, 1H), 3.80-3.68 (m, 1H), 3.59-3.56 (m, 4H), 3.23-3.14 (m, 5H), 2.86 (dd, J=16.5, 5.4 Hz, 1H), 1.50 (d, J=7.2 Hz, 3H), 1.48 (s, 9H). HRMS calcd. For $C_{17}H_{26}IN_4O_4$ [M+H]+: 477.0993, found 477.0995.

Example 5

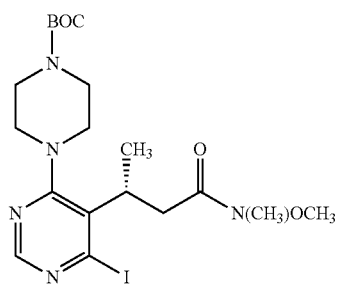

(R)-tert-butyl 4-(6-iodo-5-(4-(methoxy(methyl)amino)-4-oxobutan-2-yl)pyrimidin-4-yl)piperazine-1-carboxylate Into a solution of (R)-3-(4-(4-(tert-butoxycarbonyl)piperazin-1-yl)-6-iodopyrimidin-5-yl)butanoic acid (100 g, 210 mmol) in tetrahydrofuran (700 mL) was added 1,1'-carbonyldiimidazole (40.9 g, 252 mmol) in portions. The reaction mixture was stirred at 20° C. for 1 h and cooled to 5° C. N,O-dimethylhydroxyamine hydrochloride (41.0 g, 420 mmol) was added in portions followed by N-methylmorpholine (6.94 mL, 63.0 mmol). The mixture was stirred at 5° C. for about 1 h, slowly warmed up to room temperature, and stirred for 24 h. Saturated aqueous ammonium chloride (500 mL) and water (150 mL) were added to get a clear phase separation. The organic layer was washed with saturated aqueous ammonium chloride (500 mL) and brine (200 mL). The residual water was azeotroped off to less than 500 ppm by co-evaporation with tetrahydrofuran. The product, as a solution in tetrahydrofuran was used for the next step without further purification or isolation (weight assay yield: >99%. $^1$H NMR (300 MHz, CDCl$_3$) δ 8.23 (s, 1H), 3.84 (ddq, J=9.0, 7.2, 5.1 Hz, 1H), 3.72 (s, 3H), 3.61-3.57 (m, 4H), 3.42 (dd, J=16.5, 9.0 Hz, 1H), 3.25-3.21 (m, 4H), 3.17 (s, 3H), 2.76 (dd, J=16.5, 5.1 Hz, 1H), 1.47 (s, 9H), 1.47 (d, J=7.2 Hz, 3H). HRMS calcd. For C$_{19}$H$_{31}$IN$_5$O$_4$ [M+H]+: 520.1415, found 520.1413.

Example 6

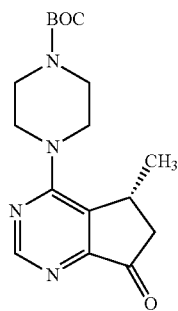 [SMILES: C[C@@H]1CC(=O)c2ncnc(N3CCN(C(=O)OC(C)(C)C)CC3)c21]

(R)-tert-butyl 4-(5-methyl-7-oxo-6,7-dihydro-5H-cyclopenta[d]pyrimidin-4-yl)piperazine-1-carboxylate Method A:

A solution of (R)-tert-butyl 4-(6-iodo-5-(4-(methyl(phenyl)amino)-4-oxobutan-2-yl)pyrimidin-4-yl)piperazine-1-carboxylate (109 g, 210 mmol) in tetrahydrofuran (600 mL) was purged with nitrogen for 30 min. Isopropyl magnesium chloride solution (159 mL, 210 mmol, 1.32 M in tetrahydrofuran) was added dropwise at −15° C. The mixture was stirred at −10° C. for 1 h and slowly transferred into a cold 20 wt % aqueous ammonium chloride (600 mL) with stirring while maintaining the internal temperature below 10° C. The organic layer was then washed with saturated aqueous ammonium chloride (500 mL). Tetrahydrofuran was distilled off at reduced pressure below 40° C. Methyl tert-butyl ether (350 mL) was slowly added while maintaining the internal temperature between 35° C. and 40° C., followed by heptane (350 mL). The mixture was slowly cooled down to 20° C. and product gradually precipitated out during the process. The slurry was filtered and the cake was dried at 40° C. under vacuum to give a gray solid (52.3 g, 75% yield over two steps). $^1$H NMR (300 MHz, CDCl$_3$) δ 8.73 (s, 1H), 3.92-3.83 (m, 2H), 3.73-3.49 (m, 7H), 2.96 (dd, J=16.5, 7.2 Hz, 1H), 2.33 (dd, J=16.5, 1.8 Hz, 1H), 1.50 (s, 9H), 1.32 (d, J=6.9 Hz, 3H). HRMS calcd. For C$_{17}$H$_{25}$N$_4$O$_3$ [M+H]+: 333.1921, found 333.1924.

Method B:

Table 1, shows example substrates that were used for preparing (R)-tert-butyl 4-(5-methyl-7-oxo-6,7-dihydro-5H-cyclopenta[d]pyrimidin-4-yl)piperazine-1-carboxylate, according to the above procedure. The compound in the Substrate column was used in place of (R)-tert-butyl 4-(6-iodo-5-(4-(methyl(phenyl)amino)-4-oxobutan-2-yl)pyrimidin-4-yl)piperazine-1-carboxylate in the above procedure, the conditions of the reaction are shown in the Scale and Conditions column, with all other conditions being substantially the same. The amount shown in the Yield column represents the area percentage of the peak of cyclized product in the crude reaction mixture as measured by HPLC-MS. The amount shown in the parenthesis represents the isolated yield. The final product, (R)-tert-butyl 4-(5-methyl-7-oxo-6,7-dihydro-5H-cyclopenta[d]pyrimidin-4-yl)piperazine-1-carboxylate, was not isolated from the below reactions.

TABLE 1

| Example Number | Substrate | Scale and Conditions | Yield % |
|---|---|---|---|
| 6.1 | (structure) | 500 mg; −20° C. | >95 (88) |
| 6.2 | (structure) | 500 mg; −20° C. | 88 |
| 6.3 | (structure) | 500 mg; −20° C. | 85 (83) |

TABLE 1-continued

| Example Number | Substrate | Scale and Conditions | Yield % |
|---|---|---|---|
| 6.4 | [BOC-piperazinyl pyrimidine with CH3, methyl ester, I] | 500 mg; −20° C. | 67 |
| 6.5 | [BOC-piperazinyl pyrimidine with CH3, COOH, I] | 500 mg; −20° C. | 90 (33) |
| 6.6 | [BOC-piperazinyl pyrimidine with Me, CONMePh, Br] | i-PrMgCl•LiCl (2.2 equiv); room temperature; 42 hr | 26 |
| 6.7 | [BOC-piperazinyl pyrimidine with Me, OMe ester, Br] | i-PrMgCl•LiCl (2.2 equiv); room temperature; 3 hr | 15 |
| 6.8 | [BOC-piperazinyl pyrimidine with Me, COOH, Br] | n-BuLi (4.0 equiv) THF, −78° C., 60 min, quenched with sat'd. NH4Cl at −78° C. | 78 |
| 6.9 | [BOC-piperazinyl pyrimidine with Me, COOH, Br] | n-BuLi (3.0 equiv) THF, −78° C., 30 min, quenched with MeOH at −78° C. | 45 |

Experiments described in Examples 1 through 6a were carried out in kilogram scales with comparable or better yields obtained.

All patents, patent applications, documents, and articles cited herein are herein incorporated by reference in their entireties.

We claim:

1. A compound of formula II or formula III:

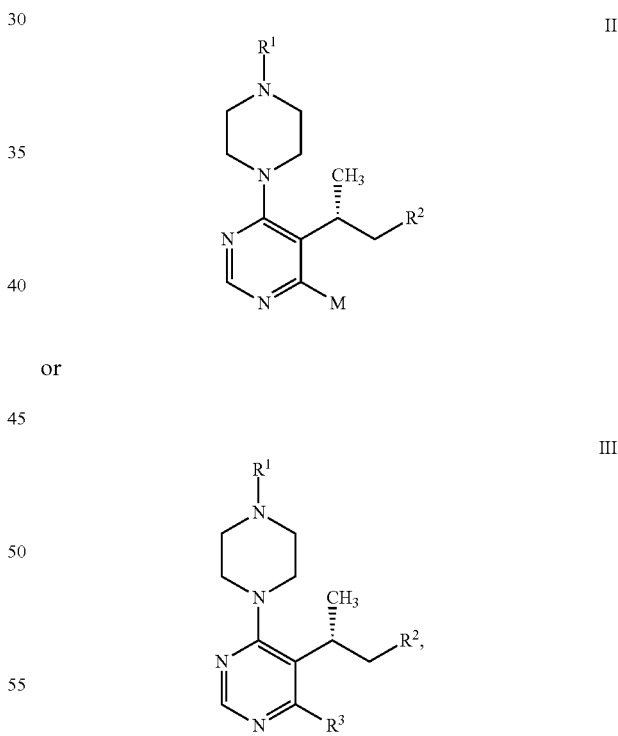

or a salt thereof, wherein:
$R^1$ is hydrogen or an amino protecting group;
$R^2$ is —CN, —COO$R^a$ or —CON$R^a R^b$;
$R^a$ and $R^b$ are independently hydrogen, —O$R^c$, substituted or unsubstituted alkyl, substituted or unsubstituted alkenyl, substituted or unsubstituted alkynyl, substituted or unsubstituted cycloalkyl, substituted or unsubstituted phenyl or substituted or unsubstituted heterocyclyl; or $R^a$ and $R^b$ are taken together with the atom to which they are attached to form a 3-7 membered heterocyclyl;

$R^c$ is independently hydrogen or optionally substituted $C_{1-12}$ alkyl;

M is Li or Mg; and $R^3$ is bromo or iodo.

2. The compound of claim 1, wherein $R^2$ —COOR$^a$ or —CONR$^a$R$^b$.

3. The compound of claim 1, wherein $R^2$ is —COOH or —COOCH$_3$.

4. The compound of claim 1, wherein $R^2$ is —C(O)N(CH$_3$)OCH$_3$.

5. The compound of claim 1, wherein $R^3$ is iodo.

6. The compound of claim 1, wherein $R^1$ is —C(O)—$R^d$ or —C(O)OR$^d$ and $R^d$ is $C_{1-6}$ alkyl or hydrogen, wherein said alkyl is optionally substituted by oxo, halo or phenyl.

7. The compound of claim 1 that is a compound of formula II:

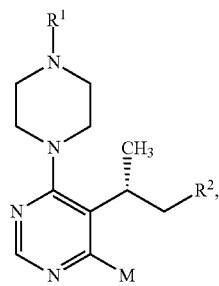

II or a salt thereof.

8. The compound of claim 7, wherein $R^1$ is a Boc group, $R^2$ is —C(O)N(R$^a$)OR$^c$, and M is Mg.

9. The compound of claim 7, wherein $R^2$ is —COOH or —COOCH$_3$.

10. The compound of claim 7, wherein $R^2$ is —C(O)N(CH$_3$)OCH$_3$.

11. The compound of claim 7, wherein $R^1$ is —C(O)—$R^d$ or —C(O)OR$^d$ and $R^d$ is $C_{1-6}$ alkyl or hydrogen, wherein said alkyl is optionally substituted by oxo, halo or phenyl.

12. The compound of claim 1 that is a compound of formula III:

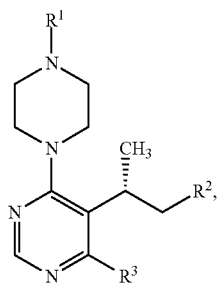

III or a salt thereof.

13. The compound of claim 12, wherein $R^1$ is hydrogen or a Boc group, $R^2$ is —CONR$^a$(OR$^c$), and $R^3$ is iodo.

14. The compound of claim 12, wherein $R^2$ is —COOH or —COOCH$_3$.

15. The compound of claim 12, wherein $R^2$ is —C(O)N(CH$_3$)OCH$_3$.

16. The compound of claim 12, wherein $R^3$ is iodo.

17. The compound of claim 12, wherein $R^1$ is —C(O)—$R^d$ or —C(O)OR$^d$ and $R^d$ is $C_{1-6}$ alkyl or hydrogen, wherein said alkyl is optionally substituted by oxo, halo or phenyl.

18. The compound of claim 1 that is (R)-tert-butyl 4-(6-iodo-5-(4-methoxy-4-oxobutan-2-yl)pyrimidin-4-yl)piperazine-1-carboxylate or a salt thereof.

19. The compound of claim 1 that is (R)-tert-butyl 4-(6-iodo-5-(4-methoxy-4-oxobutan-2-yl)pyrimidin-4-yl)piperazine-1-carboxylate.

20. The compound of claim 1 that is (R)-3-(4-(4-(tert-butoxycarbonyl)piperazin-1-yl)-6-iodo-pyrimidin-5-yl)butanoic acid or a salt thereof.

21. The compound of claim 1 that is (R)-3-(4-(4-(tert-butoxycarbonyl)piperazin-1-yl)-6-iodo-pyrimidin-5-yl)butanoic acid.

22. The compound of claim 1 that is (R)-tert-butyl 4-(6-iodo-5-(4-(methoxy(methyl)amino)-4-oxobutan-2-yl)pyrimidin-4-yl)piperazine-1-carboxylate or a salt thereof.

23. The compound of claim 1 that is (R)-tert-butyl 4-(6-iodo-5-(4-(methoxy(methyl)amino)-4-oxobutan-2-yl)pyrimidin-4-yl)piperazine-1-carboxylate.

* * * * *